United States Patent
Grez et al.

(10) Patent No.: US 9,060,595 B2
(45) Date of Patent: Jun. 23, 2015

(54) PERFORMANCE REGULATION FOR A PERSONAL CARE APPLIANCE

(71) Applicant: L'Oréal, Paris (FR)

(72) Inventors: Joseph Grez, North Bend, WA (US); Gerald Brewer, Redmond, WA (US); Kenneth Pilcher, Seattle, WA (US)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 13/917,201

(22) Filed: Jun. 13, 2013

(65) Prior Publication Data

US 2014/0367131 A1    Dec. 18, 2014

(51) Int. Cl.
*B23Q 5/00* (2006.01)
*A46B 13/00* (2006.01)

(52) U.S. Cl.
CPC ...................................... *A46B 13/00* (2013.01)

(58) Field of Classification Search
CPC ......................................................... B23Q 5/54
USPC ........ 15/21.1, 21.2, 22.1, 22.2, 22.3; 173/1–6
See application file for complete search history.

(56) References Cited

U.S. PATENT DOCUMENTS

| | | | | |
|---|---|---|---|---|
| 6,314,907 | B1 * | 11/2001 | Harris et al. .................. | 116/206 |
| 8,256,979 | B2 * | 9/2012 | Hilscher et al. ............... | 401/270 |
| 8,307,488 | B2 * | 11/2012 | Pfenniger et al. .............. | 15/22.1 |
| 2009/0031510 | A1 * | 2/2009 | Hilscher et al. ................... | 15/29 |
| 2009/0143914 | A1 * | 6/2009 | Cook et al. ..................... | 700/275 |
| 2011/0039229 | A1 * | 2/2011 | Senia ............................. | 433/131 |
| 2012/0036658 | A1 * | 2/2012 | Schaefer et al. ................. | 15/28 |
| 2012/0124758 | A1 * | 5/2012 | Sabisch et al. ................. | 15/21.1 |
| 2012/0151698 | A1 * | 6/2012 | Schaefer et al. .................. | 15/28 |
| 2014/0007362 | A1 * | 1/2014 | Park et al. ...................... | 15/22.1 |

\* cited by examiner

*Primary Examiner* — Robert Long
(74) *Attorney, Agent, or Firm* — Jensen & Puntigam, P.S.

(57) ABSTRACT

The compensating/performance regulation system includes a power skin brush having a handle, an oscillating brushhead workpiece and a drive system, wherein the brushhead workpiece has an RFID tag. An RFID reader is provided in the handle and is responsive to the RFID tag moving past the reader to produce an indication of use of the brushhead. A microprocessor calculates a value of actual use from the RFID information and uses stored information to determine the decline in performance from the calculated use. A compensating change in drive frequency or duty cycle of the drive signal is then determined by the microprocessor from stored information and transmitted to the drive system to maintain performance of the appliance.

2 Claims, 3 Drawing Sheets

PERFORMANCE REGULATION FOR A PERSONAL CARE APPLIANCE

TECHNICAL FIELD

This invention relates generally to skin care appliances and more specifically concerns a system for compensating for a degradation/decrease in performance of a workpiece portion of such an appliance.

BACKGROUND OF THE INVENTION

Power skin care appliances typically include a moving, usually oscillating, workpiece portion, such as a brush/bristle portion, also referred to as a brushhead. The brush portions gradually age, wear or become contaminated over time and with use. Further, workpieces that dispense consumable materials gradually become depleted. These gradual physical workpiece changes will result in performance decline of the appliance, either from changes in dynamic properties which produce amplitude motion differences or more directly from changes in the characteristics of the brush/bristles themselves, such as suppleness. Such brush workpieces are generally intended to be replaced when performance of the appliance no longer meets a particular standard.

Loss in performance, however, typically occurs so gradually that satisfaction with the product is also gradually reduced until the workpiece is in fact replaced. In some cases the appliance is erroneously discarded before the workpiece is replaced.

Accordingly, it is desirable that workpiece performance and the resulting experience by a user is maintained at an acceptable level until the typical time for replacement of the workpiece occurs, which typically is approximately three months.

SUMMARY OF THE INVENTION

Accordingly, a system for compensating for a decline in performance of a power skin brush, comprises: a power skin brush having a handle with a moving brushhead workpiece and a drive system therefore, the brushhead workpiece having an RFID tag; an RFID reader in the handle responsive to the RFID tag moving past the reader to produce information concerning use of the brushhead workpiece; and a microprocessor for calculating the use of the brushhead workpiece and determining any decline in performance based on said calculation of use in accordance with stored information present in the appliance, and for adjusting the frequency or duty cycle of the drive system for the appliance in accordance with the stored information to maintain performance of the appliance.

BEST MODE FOR CARRYING OUT THE INVENTION

Figure 1:
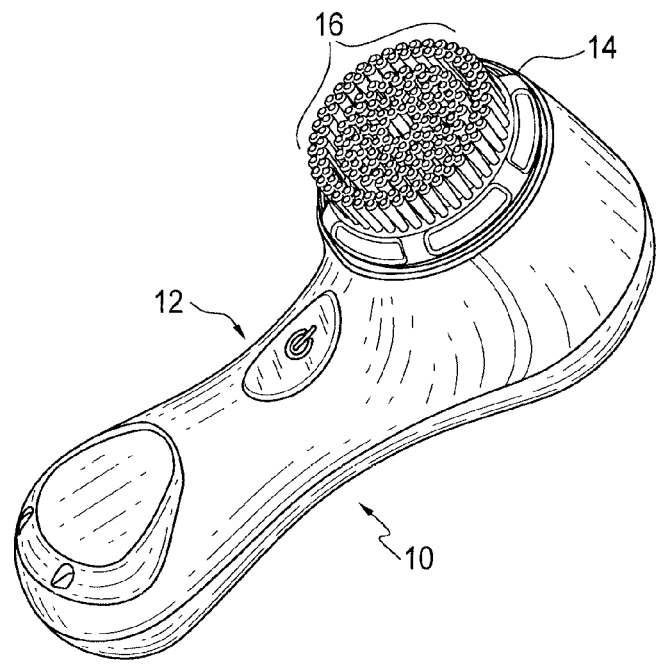
FIG. 1 shows a schematic view of a power skin brush having a replaceable brushhead.

FIG. 1 shows a power skin brush generally at 10. It includes a handle 12 and a brushhead 14 which includes a set of bristles 16. The brushhead with the set of bristles is typically conveniently replaceable. In operation, the power skin brush includes a drive assembly which includes a motor and a rechargeable battery. The drive assembly drives the brushhead assembly in a selected movement. One such movement is oscillating, with an angle/amplitude of 7° and a frequency of 176 Hz. The drive assembly is controlled by a microprocessor which includes typically both software and firmware for operating the appliance. Such an appliance is shown in more detail in U.S. Pat. No. 7,786,626 and U.S. Pat. No. 7,386,906, owned by the assignee of the present invention, the contents of which are included herein by reference. As indicated above, the performance of the skin brush will decline due to wear or other causes over time. In the present invention, the microprocessor in the handle operates to change the appliance's drive characteristics in response to accumulated use of the workpiece/brush, as discussed in detail below.

Particularly in the case of skin care brush workpieces, there are at least four known fundamental causes of workpiece degradation. These include bristle-tip wear, bristle fatigue, encrustation and dispensing depletion. With respect to non-dispensing brushheads, encrustation is the main cause of reduced brush performance. Encrustation refers to the presence of foreign material such as makeup, which bonds adjacent bristles to form a more rigid resulting structure. Stiff groups of bristles change the dynamic properties of the brush action in such a manner as to actually increase the bristle motion which is applied to the skin. As a result, there is an increase in shear force produced against the skin, due to the increase in tuft stiffness, which can be sensed as increased harshness by the user.

In the present invention, to maintain a relatively constant shear force on the skin and hence consistent performance of the appliance, a specific shift in the driving frequency and/or the duty cycle will compensate for the increase in the tuft stiffness of the bristles. The change in driving frequency and/or duty cycle is controlled over time at a rate which compensates for the encrustation rate of typical brushheads.

Figure 2:
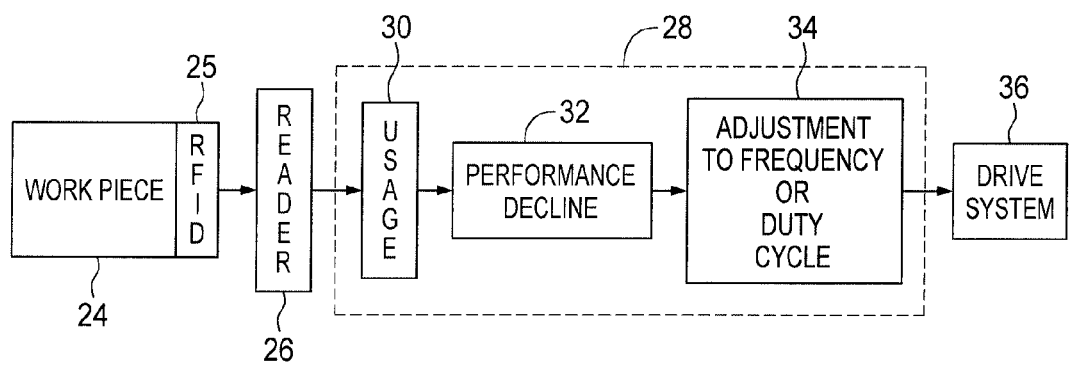
FIG. 2 is a diagram showing the system and operation of the present invention within the power skin brush of FIG. 1.

Referring to FIG. 2, the present invention includes a workpiece/brushhead 24 which includes a radio frequency identification (RFID) tag 25 positioned on the brushhead. The handle includes a reader 26 which accumulates the number of times the RFID tag passes by the reader and for accumulated time of use. This provides the information necessary to determine usage of the appliance and in particular the use of the workpiece. As indicated above, it is known that workpiece dynamic changes occur at a particular rate over time, particularly the effect due to encrustation.

The use of RFID communication and the movement of the brushhead assembly provides use/time information to the microprocessor 28. The microprocessor calculates from the RFID reader information of the amount of usage which has been accumulated, as shown at 30. This could be the actual use time or the number of use events. The usage is then correlated by the microprocessor with existing stored information, such as in a table, which relates use time to degradation in performance, as shown at 32. This information is known for a particular brushhead model. The determined value of decline of performance from table 32 is then compared with additional stored information, typically in the form of a table, which relates the determined decline in performance with the necessary adjustment to the frequency or duty cycle of the drive signal to maintain the performance of the appliance, as represented at 34. The adjustment in drive frequency or duty cycle is then transmitted in the form of a signal to the drive system 36.

Figure 3:
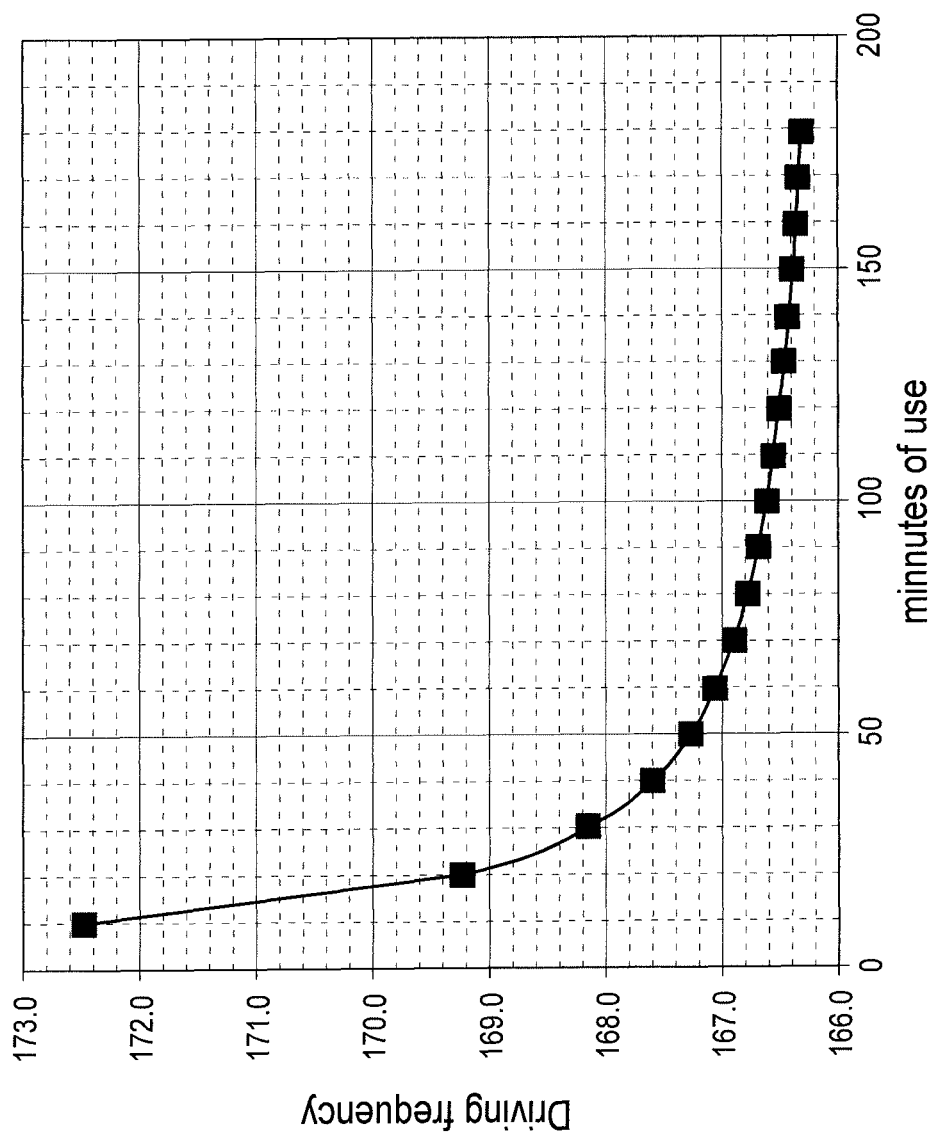
FIG. 3 is a plot/diagram of time of use versus driving frequency to maintain performance in a power skin brush.

In one example, using a standard soft brushhead, the resonant frequency of the brushhead, when wetted and loaded, is between 180 and 185 Hz. When the brushhead is fully encrusted with foreign matter, the resonant frequency typically decreases by 10 Hz to 170-175 Hz. A decline in the driving frequency of 10 Hz would maintain the original drive signal to resonance frequency relationship, thereby maintaining performance of the appliance at an original level. FIG. 3 shows the relationship of frequency to minutes of use. For a particular brushhead, the decline in performance follows an exponential curve. Each particular brushhead type will have such a known relationship, which is stored in the microprocessor or other memory within the handle of the appliance.

Figure 4:
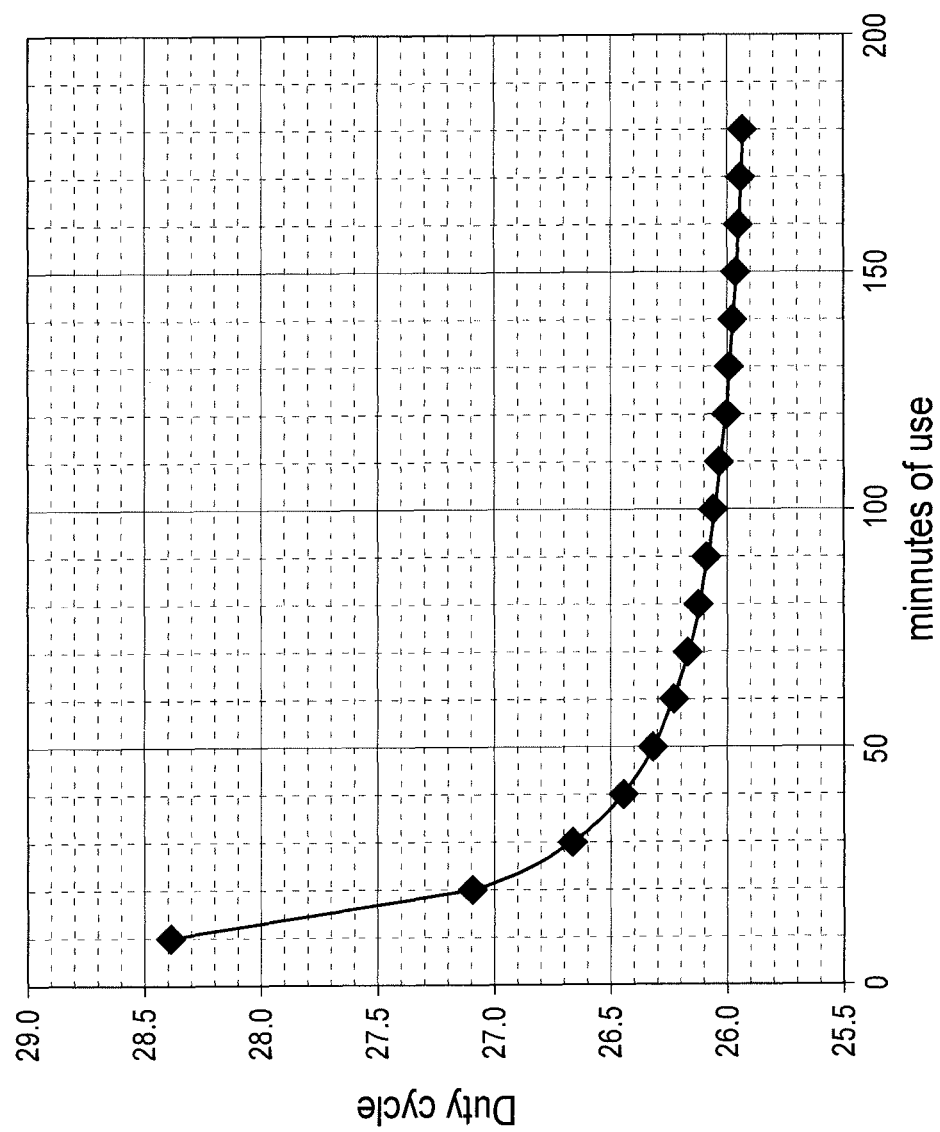
FIG. 4 is plot/diagram of time of use versus duty cycle relative to maintain performance of a power skin brush.

The compensation can also be accomplished via a shift in duty cycle. Using a standard soft brush as an example, at a fixed duty cycle, the loaded amplitude of motion of the brushhead when wetted and loaded is approximately 7° peak to peak. When the brushhead is fully encrusted with foreign material the same duty cycle loading at resonance produces an amplitude of 8°. By lowering the duty cycle by 14%, as one example for a particular appliance. The amplitude is decreased to 7°, the original amplitude. In this example, for an initial duty cycle of 30%, the new duty cycle would be 25.8%. A plot of duty cycle v. time is shown in FIG. 4. Again, like the drive frequency plot, the decline in duty cycle to maintain performance is exponential. The plots of drive frequency v. time and duty cycle v. time are both stored in the appliance.

The above compensation system maintains the performance of the brushhead over a specific time, e.g. approximately three months, which is a normal usage time for a brushhead for a skin brush appliance. At the end of such a time, a signal in or from the appliance or other means can be used to indicate that the brushhead needs to be replaced. The change in drive frequency or duty cycle can be accomplished continuously or at specific times during the usage life. Preferably, the change will occur upon each use of the appliance. Although, as indicated above, the primary cause of performance decline is encrustation, other factors of decline can be the subject of performance compensation as well. This can be important for those brushes typically used in a manner that does not cause encrustation. The stored information in the appliance can account for various causes of decline in performance. The compensated appliance provides consistent performance over the typical period of useful life of the replaceable brushhead. When the typical period of useful life terminates, the brushhead can be appropriately replaced. This arrangement assures consistent performance and prevents premature replacement of brushheads and/or erroneous replacement of the appliance due to uncompensated performance decline.

Although a preferred embodiment of the invention has been disclosed for purposes of illustration, it should be understood that various changes, modifications and substitutions may be incorporated in the embodiment without departing from the spirit of the invention, which is defined by the claims which follow.

What is claimed is:

1. A system for compensating for a decline in performance of a power skin brush appliance, comprising:
   a power skin brush having a handle with an oscillating brushhead/workpiece and a drive system therefor, the brushhead/workpiece having an RFID tag;
   an RFID reader in the handle responsive to the RFID tag moving cyclically past the reader to produce information concerning time of actual use or the actual number of individual use events of the brushhead/workpiece; and
   a microprocessor for calculating the time of actual use or the actual number of individual use events of the brushhead/workpiece and determining any decline in performance based on said calculation of the time of actual use or the actual number of use events in accordance with stored information present in the appliance, and for adjusting the frequency or duty cycle of the drive system for the appliance in accordance with the stored information to maintain performance of the appliance.

2. A system of claim 1, including a system for indicating when the brushhead/workpiece should be replaced.

* * * * *